(12) United States Patent
Yanagihara et al.

(10) Patent No.: US 12,383,126 B2
(45) Date of Patent: Aug. 12, 2025

(54) SURGERY SYSTEM AND CONTROL METHOD FOR SURGERY SYSTEM TO ADJUST POSITION AND ORIENTATION OF IMAGER

(71) Applicant: OLYMPUS CORPORATION, Tokyo (JP)

(72) Inventors: Masaru Yanagihara, Tokyo (JP); Ryota Sasai, Tokyo (JP); Masafumi Haraguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 45 days.

(21) Appl. No.: 18/209,854

(22) Filed: Jun. 14, 2023

(65) Prior Publication Data
US 2023/0320793 A1     Oct. 12, 2023

Related U.S. Application Data

(63) Continuation of application No. PCT/JP2021/006642, filed on Feb. 22, 2021.

(51) Int. Cl.
*A61B 1/045* (2006.01)
*A61B 1/01* (2006.01)
(Continued)

(52) U.S. Cl.
CPC ............ *A61B 1/045* (2013.01); *A61B 1/01* (2013.01); *A61B 34/20* (2016.02); *A61B 34/25* (2016.02);
(Continued)

(58) Field of Classification Search
CPC ...... A61B 2090/364; A61B 2090/3983; A61B 2090/363; A61B 90/361; A61B 90/37;
(Continued)

(56) References Cited

U.S. PATENT DOCUMENTS

2005/0027304 A1* 2/2005 Leloup ............... A61B 17/1725
                                                                 606/102
2007/0225550 A1* 9/2007 Gattani ................. A61B 90/37
                                                                 600/101
(Continued)

FOREIGN PATENT DOCUMENTS

DE     112016005720 T5 *  9/2018  ............... A61B 6/12
EP         2169346 A1 *  3/2010  ............. A61B 34/20
(Continued)

OTHER PUBLICATIONS

WIPO International Bureau, Written Opinion for PCT/JP2021/006642 (Apr. 27, 2021) (Year: 2021).*
(Continued)

*Primary Examiner* — David N Werner
(74) *Attorney, Agent, or Firm* — Scully, Scott, Murphy & Presser, P.C.

(57) ABSTRACT

A surgery system includes: an imager capturing an image of a treatment target; a display having a screen displaying the image of the treatment target captured by the imager; and a processor configured to control a display area of the treatment target on the screen, wherein the processor is configure to: calculate a position of a resection end section of the treatment target on the basis of the image of the treatment target acquired by the imager; cause the display area of the treatment target to be moved to a position at which the resection end section is disposed at a prescribed reference position on the screen; calculate an orientation of a marking added to the treatment target on the screen; and cause the display area of the treatment target to be rotated to an orientation in which the marking is disposed in a prescribed reference orientation on the screen.

20 Claims, 11 Drawing Sheets

(51) Int. Cl.
    *A61B 34/00*     (2016.01)
    *A61B 34/20*     (2016.01)
    *A61B 90/00*     (2016.01)
    *G06T 7/00*     (2017.01)
    *G06T 7/73*     (2017.01)
    *H04N 23/695*     (2023.01)
    *A61B 34/10*     (2016.01)

(52) U.S. Cl.
    CPC ............ *A61B 90/361* (2016.02); *A61B 90/37* (2016.02); *G06T 7/0012* (2013.01); *G06T 7/73* (2017.01); *H04N 23/695* (2023.01); *A61B 2034/107* (2016.02); *A61B 2034/2046* (2016.02); *A61B 2034/2055* (2016.02); *A61B 2034/2065* (2016.02); *A61B 2034/2068* (2016.02); *A61B 2034/2074* (2016.02); *A61B 2034/252* (2016.02); *A61B 2034/254* (2016.02); *A61B 2034/256* (2016.02); *A61B 2090/363* (2016.02); *A61B 2090/372* (2016.02); *A61B 90/39* (2016.02); *A61B 2090/3937* (2016.02); *G06T 2207/10068* (2013.01); *G06T 2207/30204* (2013.01)

(58) Field of Classification Search
    CPC ....... A61B 90/39; A61B 90/3937; A61B 1/01; A61B 1/045; A61B 2034/2046; A61B 2034/2055; A61B 2034/2074; A61B 2034/2065; A61B 2034/2068; A61B 34/20; A61B 34/25; A61B 2034/107; A61B 2034/254; A61B 2034/256
    See application file for complete search history.

(56) References Cited

U.S. PATENT DOCUMENTS

| | | | |
|---|---|---|---|
| 2008/0114334 A1 | 5/2008 | Voegele | |
| 2011/0218550 A1* | 9/2011 | Ma | A61B 17/07207 606/130 |
| 2016/0353970 A1 | 12/2016 | Inoue | |
| 2017/0258526 A1* | 9/2017 | Lang | A61B 17/1742 |
| 2018/0098049 A1* | 4/2018 | Sugano | G16H 20/40 |
| 2018/0158209 A1* | 6/2018 | Fine | G16H 30/40 |
| 2019/0223957 A1* | 7/2019 | Dekel | A61C 9/004 |
| 2019/0231442 A1* | 8/2019 | Saget | A61F 2/46 |
| 2019/0254563 A1* | 8/2019 | Nakamitsu | A61B 5/7445 |
| 2019/0365499 A1 | 12/2019 | Nagao et al. | |
| 2020/0046208 A1 | 2/2020 | Kasai et al. | |
| 2020/0059640 A1* | 2/2020 | Browd | A61B 1/000094 |
| 2020/0138518 A1* | 5/2020 | Lang | A61B 17/1666 |
| 2020/0146754 A1* | 5/2020 | Row | A61B 34/30 |
| 2020/0367733 A1 | 11/2020 | Kihara et al. | |
| 2021/0204963 A1* | 7/2021 | Mitra | A61B 17/157 |
| 2021/0369355 A1* | 12/2021 | Masaki | A61B 5/6852 |
| 2022/0031422 A1* | 2/2022 | Wood | A61B 1/00193 |
| 2022/0398755 A1* | 12/2022 | Herrmann | G16H 30/40 |
| 2022/0409326 A1* | 12/2022 | Wright | G06V 10/82 |
| 2023/0017738 A1* | 1/2023 | Elliott-Bowman | A61B 1/00039 |
| 2023/0157525 A1* | 5/2023 | Hunter | A61B 1/045 600/102 |

FOREIGN PATENT DOCUMENTS

| | | | | |
|---|---|---|---|---|
| EP | 3 108 795 A1 | 12/2016 | | |
| JP | 2015-154803 A | 8/2015 | | |
| JP | 2016513540 A | * | 5/2016 | ............ A61B 90/00 |
| JP | 6629186 B2 | 1/2020 | | |
| WO | 2014/181222 A1 | 11/2014 | | |
| WO | 2018/159155 A1 | 9/2018 | | |
| WO | 2018/159328 A1 | 9/2018 | | |
| WO | WO-2019032143 A1 | * | 2/2019 | .......... A61B 1/0004 |
| WO | 2019/163890 A1 | 8/2019 | | |
| WO | WO-2019187449 A1 | * | 10/2019 | |

OTHER PUBLICATIONS

International Search Report dated Apr. 27, 2021 received in PCT/JP2021/006642.

* cited by examiner

SURGERY SYSTEM AND CONTROL METHOD FOR SURGERY SYSTEM TO ADJUST POSITION AND ORIENTATION OF IMAGER

This is a continuation of International Application PCT/JP2021/006642 which is hereby incorporated by reference herein in its entirety.

TECHNICAL FIELD

The present invention relates to a surgery system and a control method for the surgery system.

BACKGROUND ART

In the related art, there is a known surgery system that moves an endoscope by means of a robot (for example, see Patent Literature 1). In the case in which an anatomical feature, such as a blood vessel of the heart, is covered with fat or in the case in which the anatomical feature is positioned outside the field of view of an endoscope, the anatomical feature does not appear in an endoscope image. Patent Literature 1 discloses a technology that visualizes an anatomical feature by determining the pose of an endoscope on the basis of the anatomical feature in a pre-surgery image and by disposing, via robot control, the endoscope in the determined pose.

CITATION LIST

Patent Literature

{PTL 1} Publication of Japanese Patent No. 6629186

SUMMARY OF INVENTION

An aspect of the present invention is a surgery system including: an imager that captures an image of a treatment target; a display having a screen that displays the image of the treatment target captured by the imager; and a processor comprising hardware, the processor being configured to control a display area of the treatment target displayed on the screen, wherein the processor is configure to: calculate a position of a resection end section of the treatment target on the basis of the image of the treatment target acquired by the imager; cause the display area of the treatment target to be moved to a position at which the resection end section is disposed at a prescribed reference position on the screen; calculate an orientation of a marking added to the treatment target on the screen; and cause the display area of the treatment target to be rotated to an orientation in which the marking is disposed in a prescribed reference orientation on the screen.

Another aspect of the present invention is a control method executed by a processor, which includes hardware, of a surgery system, the surgery system including an imager that captures an image of a treatment target and a display having a screen that displays the image of the treatment target captured by the imager, and the method including: calculating a position of a resection end section of the treatment target on the basis of the image of the treatment target acquired by the imager; causing a display area of the treatment target to be moved to a position at which the resection end section is disposed at a prescribed reference position on the screen; calculating an orientation of a marking added to the treatment target on the screen; and causing the display area of the treatment target to be rotated to an orientation in which the marking is disposed in a prescribed reference orientation on the screen.

Further another aspect of the present invention is a control method executed by a processor, which includes hardware, of a surgery system, the surgery system including an imager that captures an image of a treatment target and a display having a screen that displays the image of the treatment target captured by the imager, and the method including: calculating a position of a resection end section of the treatment target on the basis of the image of the treatment target acquired by the imager; and causing, by processing the image, a display area of the treatment target to be moved to a position at which the resection end section is disposed at a prescribed reference position on the screen.

DESCRIPTION OF EMBODIMENT

A surgery system and a control method for the surgery system according to an embodiment of the present invention will be described below with reference to the drawings.

[Configuration of Surgery System 100]

A surgery system 100 according to this embodiment is a system that assists treatment by means of an endoscope 1 and a treatment tool 5 in a laparoscopic surgery. The surgery system 100 has a function for autonomously controlling the endoscope 1 and has, in particular, an autonomous movement function for optimizing the field of view for different surgery scenes by moving the endoscope 1.

Figure 1:
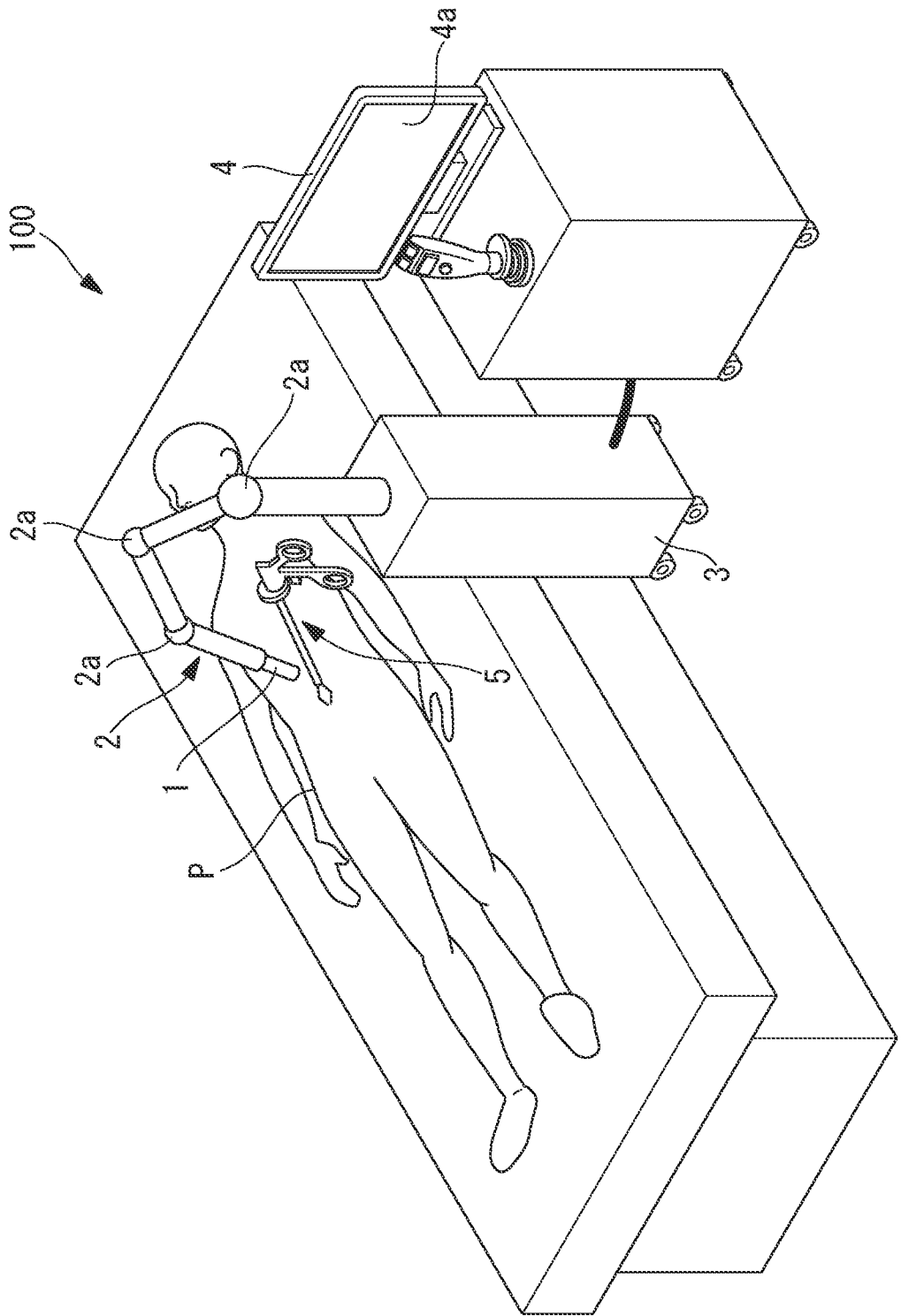
FIG. 1 is an external view of the overall configuration of a surgery system according to an embodiment of the present invention.

As shown in FIG. 1, the surgery system 100 includes: the endoscope 1 that serves as an image acquisition device for capturing images of a treatment target A inside the body of a patient P; a moving device 2 that moves the endoscope 1; a control device 3 that controls the endoscope 1 and the moving device 2; and a display device 4 that displays the images of the treatment target A captured by the endoscope 1. Note that the image acquisition device is not limited to the endoscope 1 and may be an arbitrary device that captures images of the treatment target A inside the body of the patient P.

The endoscope 1 is a rigid endoscope, and a distal-end section of the endoscope 1 is provided with a lens and an element, such as an image-acquisition element, for capturing images of the treatment target A, such as an organ or tissue. The endoscope 1 is connected to the control device 3 with a signal line that passes through the interior of the moving device 2, receives control signals for controlling the endoscope 1 from the control device 3, and transmits endoscope image data to the control device 3.

The moving device 2 is an electrically driven robot arm having at least one flexing joint 2a, and a proximal-end section of the endoscope 1 is connected to a distal-end section of the robot arm 2.

The display device 4 is a publicly known display device, such as a liquid crystal display, and has a screen 4a. The display device 4 is connected to the control device 3 and displays the endoscope images of the treatment target A input thereto from the control device 3 on the screen 4a. The display device 4 may be a head mounted display or a projector.

The endoscope 1 is moved as a result of flexing motions of the joint 2a of the robot arm 2, and, accordingly, the field of view of the endoscope 1, in other words, a display area of the treatment target A displayed on the screen 4a, is moved. The motion of the robot arm 2 is controlled by the control device 3.

Figure 2:
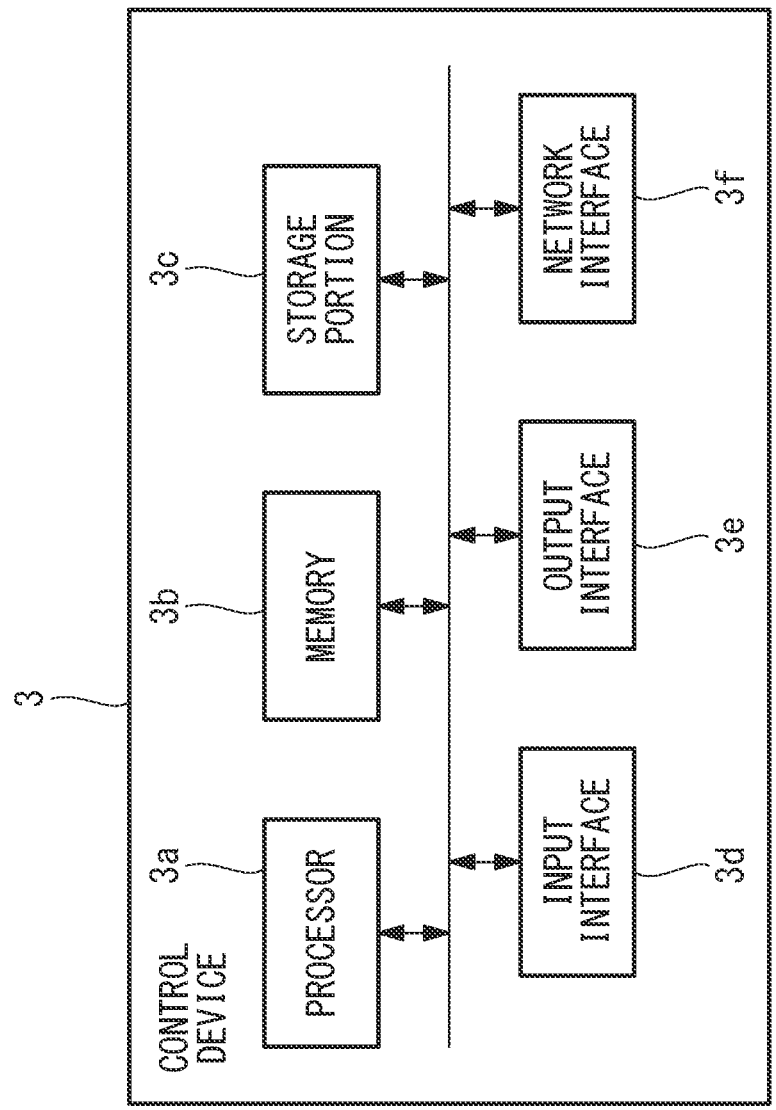
FIG. 2 is a block diagram showing the configuration of a control device of the surgery system in FIG. 1.

As shown in FIG. 2, the control device 3 includes at least one processor 3a, such as a central processing unit, a memory 3b, a storage portion 3c, an input interface 3d, an output interface 3e, and a network interface 3f.

The endoscope images transmitted from the endoscope 1 are sequentially input to the control device 3 via the input interface 3d and are sequentially output to the display device 4 via the output interface 3e. Accordingly, the endoscope images of the treatment target A captured by the endoscope 1 are displayed on the screen 4a.

The storage portion 3c is a ROM (read-only memory) or a non-volatile recording medium, such as a hard disk, and stores programs and data required to cause the processor 3a to execute processing. The programs are read into the memory 3b and executed by the processor 3a to realize functions of the control device 3, described later. Some of the functions of the control device 3 may be realized by means of a dedicated logic circuit or the like.

Figure 3A:
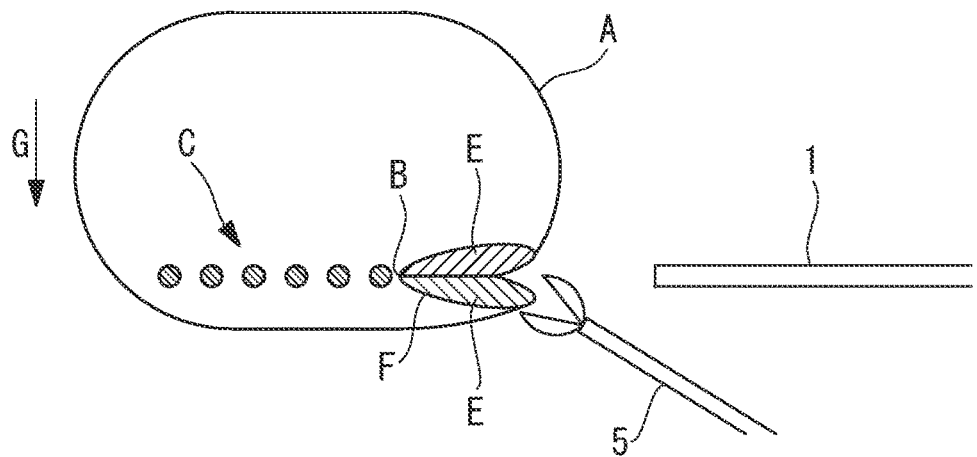
FIG. 3A is a diagram showing the initial state of resecting a treatment target.
Figure 3B:
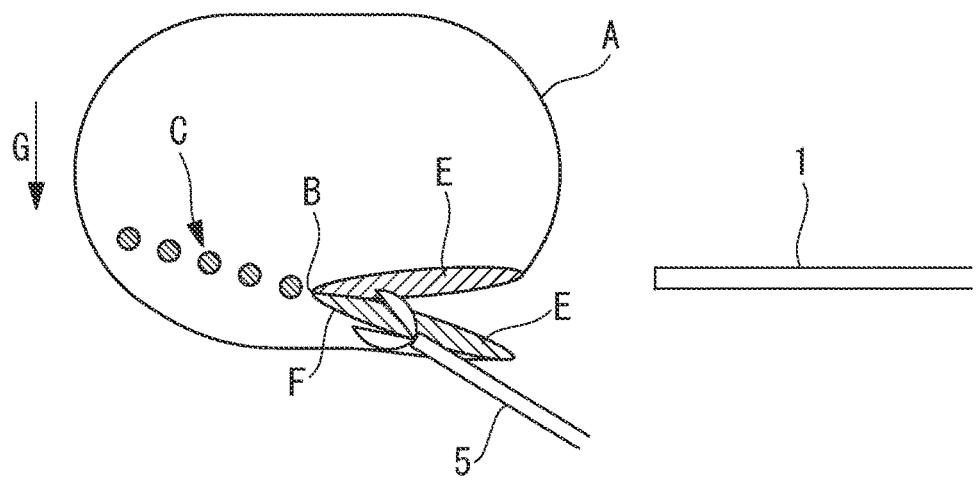
FIG. 3B is a diagram showing a state in which the treatment target has deformed as the resecting progresses.
Figure 3C:
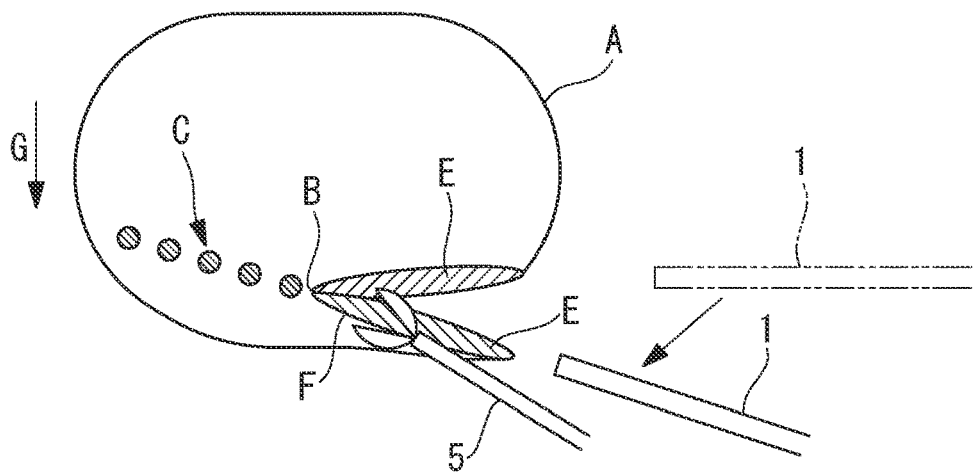
FIG. 3C is a diagram showing a state in which an endoscope has been moved to an appropriate position and orientation with respect to a resection end section and a marking.
Figure 4A:
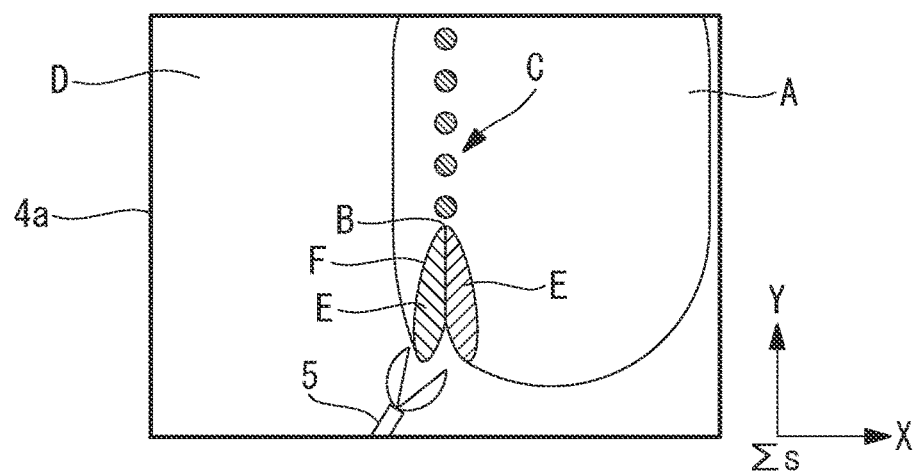
FIG. 4A is an endoscope image of the treatment target in FIG. 3A.
Figure 4B:
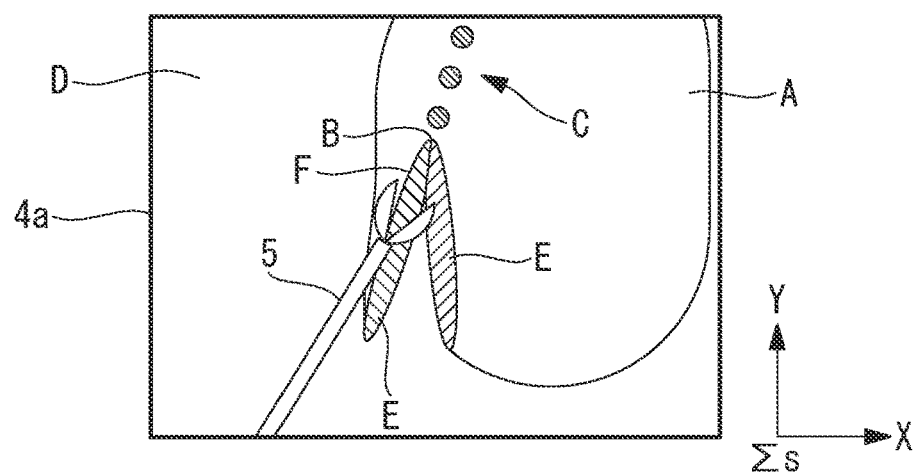
FIG. 4B is an endoscope image of the treatment target in FIG. 3B.

As shown in FIGS. 3A and 3B, in a surgery, such as hepatectomy, in which the treatment target A is resected, due to the influence of gravity G and the influence of the softness of the treatment target A, the treatment target A is at least partially deformed or moved as the resecting progresses. As a result, as shown in FIGS. 4A and 4B, there are cases in which the position, the orientation, and the size of a display area of the treatment target A on the screen 4a gradually change. FIGS. 3A to 3C show hepatectomy in which parenchyma of the liver, serving as the treatment target A, is resected. In FIGS. 3A to 3C, gravity G acts in the direction toward the bottom from the top in the plane of the drawings.

The control device 3 calculates a first feature value, a second feature value, and a third feature value. The first feature value is a value representing the composition of the treatment target A on the screen 4a. The second feature value is a value representing the orientation of the treatment target A on the screen 4a. The third feature value is a value representing the size of the display area of the treatment target A displayed on the screen 4a, in other words, the size of the field of view of the endoscope 1.

Specifically, the control device 3 calculates the position of a resection end section B on the screen 4a so as to serve as the first feature value. The resection end section B is a distal-end section of a resection line formed by the treatment tool 5. The position of the resection end section B is represented by the coordinates of the resection end section B in a screen coordinate system $\Sigma s$ fixed on the screen 4a. In addition, the control device 3 calculates the orientation of a marking C on the screen 4a (that is, the rotation angle of the marking C in the plane along the screen 4a) so as to serve as the second feature value. The marking C is a planned resection line added to an outer surface of the treatment target A before resecting the treatment target A, and is, for example, a dotted line or a solid line. The marking C is added, for example, by cauterizing the outer surface of the treatment target A by means of an electric scalpel. Also, the control device 3 calculates the distance between a distal end of the endoscope 1 and the resection end section B so as to serve as the third feature value.

The specific calculation methods for the respective feature values will be described in detail later.

The control device 3 loads one endoscope image from among the endoscope images that are sequentially input thereto and calculates the aforementioned first feature value, second feature value, and third feature value on the basis of the loaded endoscope image. Subsequently, the control device 3 controls the robot arm 2 on the basis of the calculated first, second, and third feature values, thereby causing the field of view of the endoscope 1 to be moved so that the respective feature values become roughly equal to prescribed references. Accordingly, the treatment target A is continuously displayed on the screen 4a in accordance with the prescribed references.

In addition, before calculating the feature values and causing the field of view of the endoscope 1 to be moved, the control device 3 sets the prescribed references on the basis of an endoscope image D. The setting methods for the prescribed references will be described in detail later.

[Control Method for Surgery System 100]

Next, a control method for the surgery system 100 executed by the control device 3 will be described.

Figure 5A:
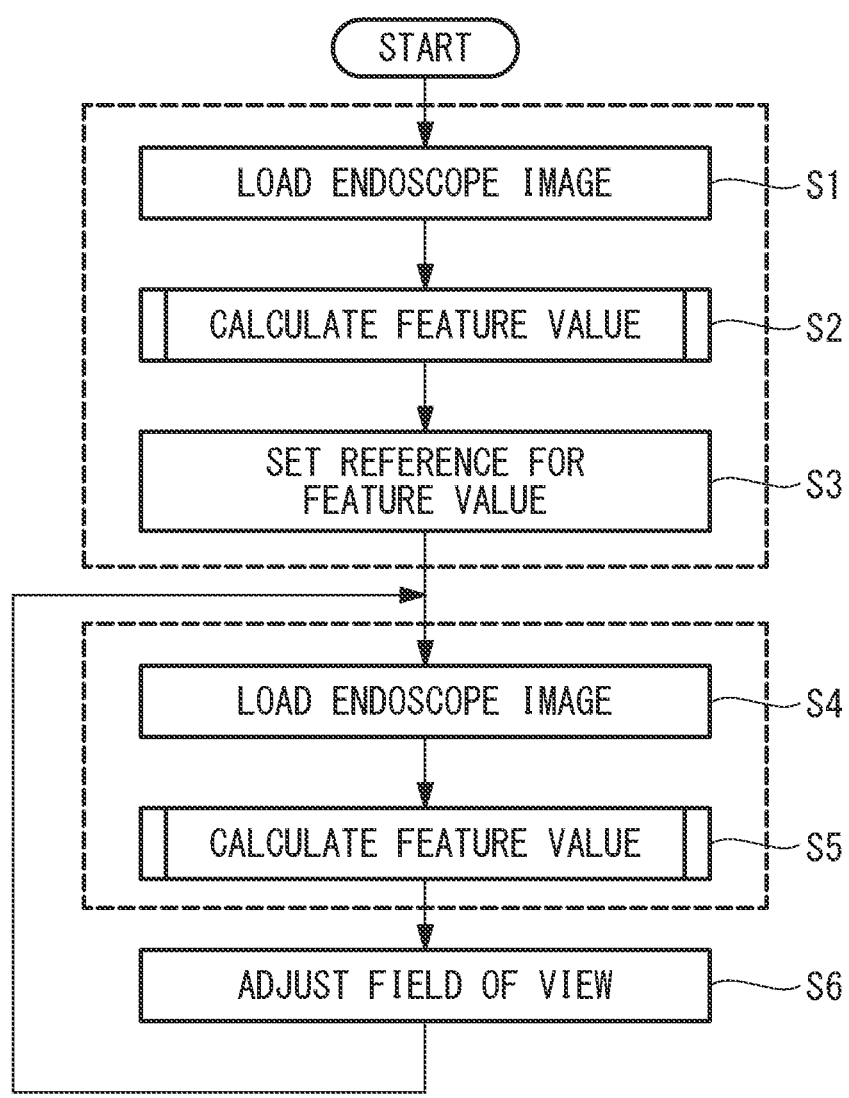
FIG. 5A is a flowchart of a control method for the surgery system in FIG. 1.

As shown in FIG. 5A, the control method for the surgery system 100 includes: reference setting steps S1 to S3 of setting a reference for each of the three feature values; feature-value calculating steps S4 and S5 of calculating the three feature values on the basis of the endoscope image D; and a field-of-view adjusting step S6 of adjusting the field of view of the endoscope 1 by controlling the moving device 2.

The reference setting steps include: step S1 of loading the endoscope image D; step S2 of calculating the three feature values; and step S3 of setting the references for the respective feature values.

In step S1, the control device 3 loads one endoscope image D from among the endoscope images D sequentially input thereto. As shown in FIG. 4A, the endoscope image D loaded at this time is an image captured before the resection end section B and the marking C are moved due to deformation of the treatment target A. The loading of the image is executed, for example, in response to an operator making an input to the control device 3.

Figure 5B:
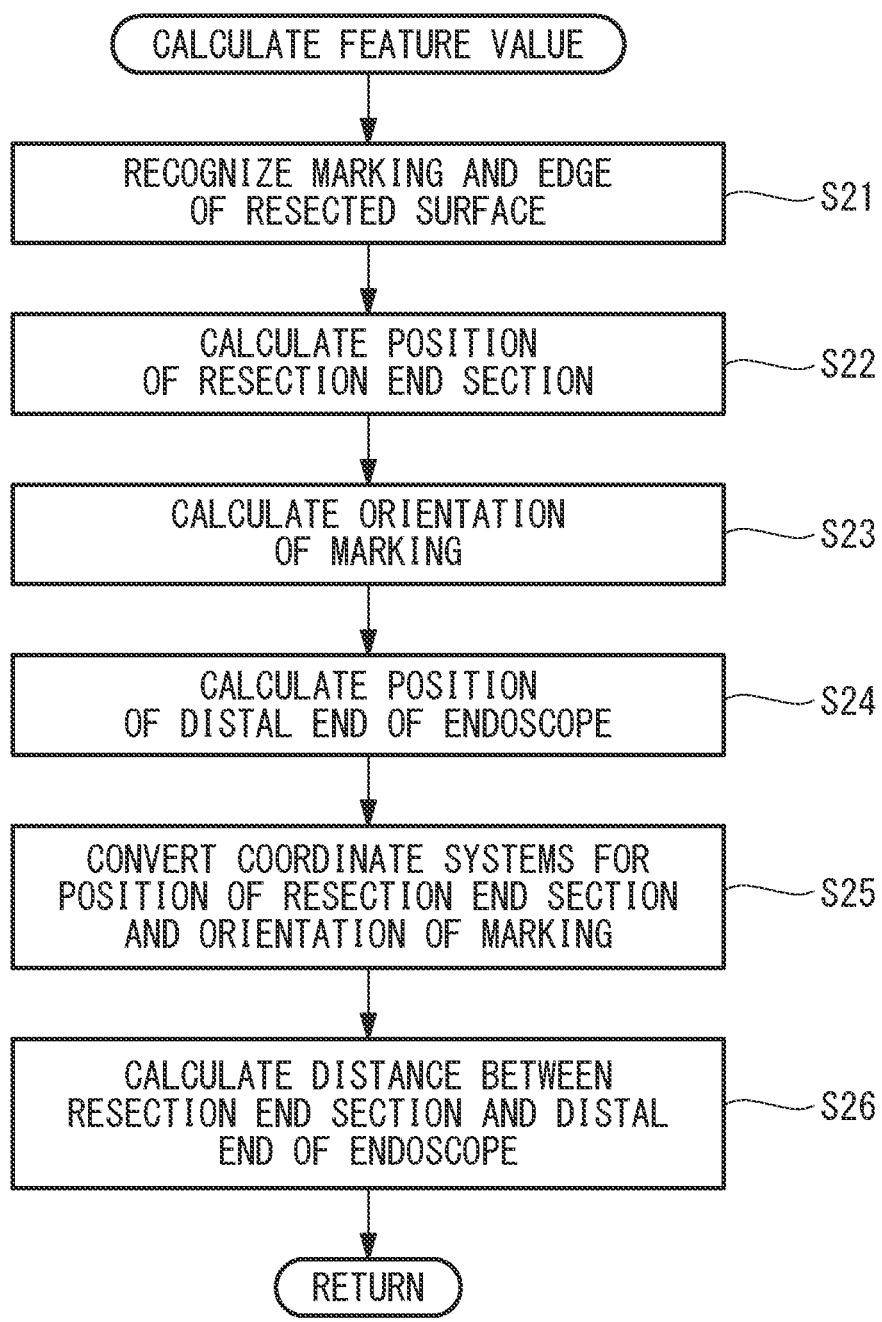
FIG. 5B is a flowchart of a feature-value calculation routine in FIG. 5A.

Next, in step S2, the three feature values are respectively calculated on the basis of the loaded endoscope image D. Specifically, as shown in FIG. 5B, step S2 includes: step S21 of recognizing the marking C and edges F of resected surfaces E in the endoscope image D; step S22 of calculating the first feature value; step S23 of calculating the second feature value; and steps S24 to S26 of calculating the third feature value.

Figure 6:
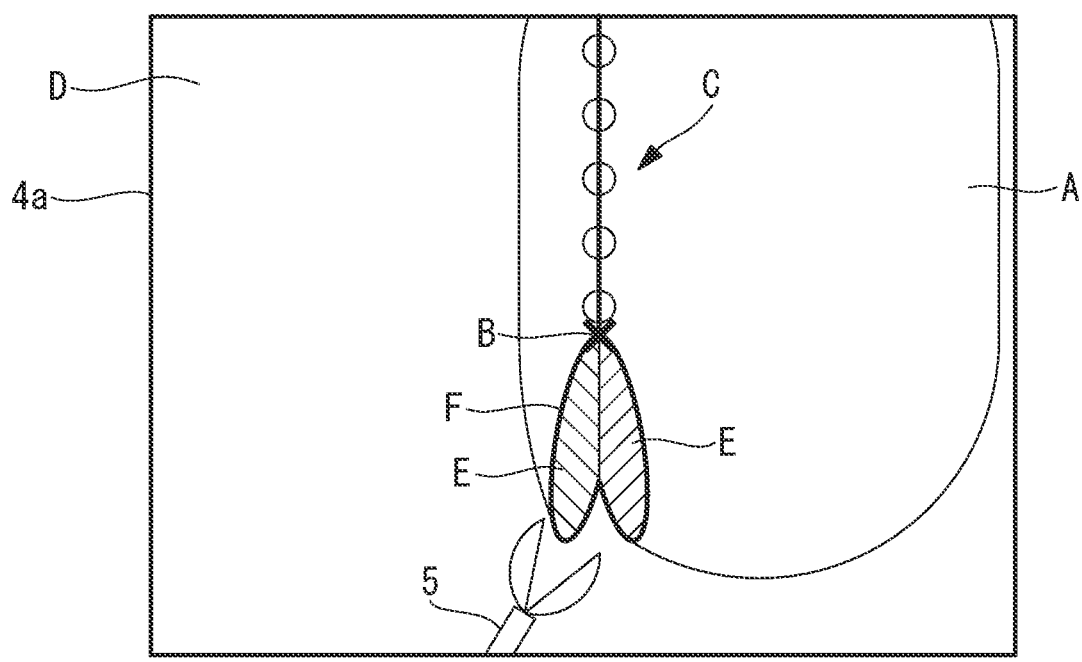
FIG. 6 is a diagram for explaining a calculation method for the resection end section.

In step S21, the control device 3 recognizes the marking C and the edges F of the resected surfaces E by applying image processing to the endoscope image D, as shown in FIG. 6. Because the marking C and the resected surfaces E have different colors from an outer surface of the treatment target A and peripheral tissue, the control device 3 can recognize the marking C and the resected surfaces E on the basis of the colors thereof. At this time, it is difficult to recognize the resected surfaces E on two sides separately from each other by means of the image processing, and the resected surfaces E on the two sides are recognized as one surface. Therefore, the edges F are recognized as a single line.

Next, in step S22, the control device 3 calculates the position of an intersection between the marking C and the edge F on the screen 4a so as to serve as the position of the resection end section B. The position of the resection end section B is represented as the coordinates in the screen coordinate system Σs.

In the case in which the marking C is a dotted line, as shown in FIG. 6, a solid line that connects dots with each other may be generated and the position of the intersection between the solid line and the edge F may be calculated.

In addition, in the case in which a closed circle-like edge F or a plurality of edges F are recognized, the positions of a plurality of intersections could be calculated. In this case, the position of an intersection closest to the marking C may be employed as the position of the resection end section B.

Next, in step S23, the control device 3 detects the positions of two arbitrary points that are different from each other in the marking C on the screen 4a. The positions of the two points are represented as the coordinates in the screen coordinate system Σs. Subsequently, the control device 3 calculates a vector connecting the two points so as to serve as the orientation of the marking C on the screen 4a.

The order of steps S22 and S23 is arbitrary, and step S22 may be executed after step S23.

Next, in step S24, the control device 3 detects the position of the distal end of the endoscope 1 in a base coordinate system Σr of the robot holding the endoscope 1. The base coordinate system Σr is a coordinate system that is fixed with respect to an immobile portion (for example, a proximal-end section of the robot arm 2) of the robot arm 2. For example, the control device 3 acquires the rotation angles of the respective joints 2a by means of angle sensors provided in the respective joints 2a of the robot arm 2 and detects the position of the distal end of the endoscope 1 on the basis of the rotation angles. The position of the distal end of the endoscope 1 is represented as the coordinates in the base coordinate system Σr of the robot.

Next, in step S25, the control device 3 converts the position of the resection end section B calculated in step S22 to the position in the base coordinate system Σr of the robot. In addition, the control device 3 converts the orientation of the marking C calculated in step S23 to the orientation in the base coordinate system Σr of the robot.

Next, in step S26, the control device 3 calculates the distance between the position of the distal end of the endoscope 1 and the position of the resection end section B obtained in steps S24 and S25 and stores the calculated distance in the storage portion 3c. In addition, the control device 3 stores the position of the resection end section B and the orientation of the marking C converted in step S25 in the storage portion 3c.

Next, in step S3, the control device 3 sets the position of the resection end section B stored in the storage portion 3c to be a prescribed reference position that serves as the reference for the first feature value. In addition, the control device 3 sets the orientation of the marking C stored in the storage portion 3c to be a prescribed reference orientation that serves as the reference for the second feature value. In addition, the control device 3 sets the distance stored in the storage portion 3c to be a prescribed reference distance that serves as the reference for the third feature value.

Next, the feature-value calculating steps are performed. The feature-value calculating steps include: step S4 of re-loading an endoscope image D; and step S5 of re-calculating the three feature values on the basis of the loaded endoscope image D.

In step S4, the control device 3 re-loads an endoscope image D. As shown in FIG. 4B, the endoscope image D loaded at this time is an endoscope image captured after some time has passed from when the endoscope image D loaded in step S1 was captured, that is, an endoscope image captured after the resecting has progressed.

Next, in step S5, the control device 3 calculates the three feature values by performing the same processing as in steps S21 to S26 on the basis of the re-loaded endoscope image D.

Next, in the field-of-view adjusting step S6, the control device 3 compares the three feature values calculated in step S5 with the respective references and calculates amounts by which the respective feature values have changed from the references. Next, the control device 3 calculates a target position and a target pose of the endoscope 1 at which the amounts of change in the respective feature values become zero and the respective feature values become roughly equal to the references. In other words, the target position and the target pose are the position and the pose of the endoscope 1 at which the resection end section B is disposed at the reference position on the screen 4a, the marking C is disposed in the reference orientation on the screen 4a, and the distance from the resection end section B to the distal end of the endoscope 1 is equal to the reference distance.

Next, the control device 3 calculates movement amounts and movement directions of the endoscope 1 for moving the endoscope 1 to the target position and the target pose and calculates motion amounts (specifically, the rotation amounts of the respective joints 2a) of the robot arm 2 for achieving the calculated movement amounts and movement directions. Subsequently, the control device 3 generates control signals for causing the robot arm 2 to perform motions in amounts corresponding to the calculated motion amounts and transmits the control signals to the robot arm 2.

Figure 4C:
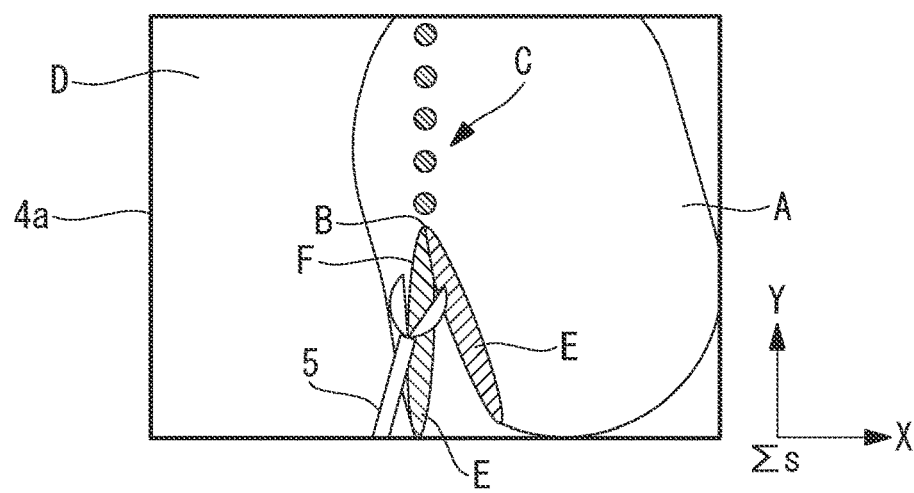
FIG. 4C is an endoscope image of the treatment target in FIG. 3C.

Accordingly, as shown in FIG. 3C, the robot arm 2 performs motions in response to the control signals. Consequently, the endoscope 1 is moved, in the abdominal cavity, to the target position and the target pose at which the changes in the three feature values are canceled out and the field of view of the endoscope 1 is moved. As a result, as shown in FIG. 4C, the display area of the treatment target A displayed on the screen 4a is moved and rotated, the resection end section B is disposed at the prescribed reference position, and the marking C is disposed in the prescribed reference orientation. In addition, the distance from the distal end of the endoscope 1 to the resection end section B is adjusted so as to be the prescribed reference distance, and thus, the size of the display area of the treatment target A displayed on the screen 4*a* is maintained at a prescribed size.

As has been described above, with this embodiment, when the treatment target A, such as the liver, deforms as the resecting thereof progresses and the feature values change, the endoscope 1 is automatically moved to the position and the orientation at which the changes in the feature values are cancelled out. In other words, the field of view of the endoscope 1 is automatically moved so as to follow the movements of the resection end section B and the marking C. Accordingly, while the treatment target A is being resected along the marking C, the position of the resection end section B, the orientation of the marking C, and the size of the field of view are maintained at the respective references. For example, the position of the resection end section B is continuously displayed at the center of the screen 4*a* and the marking C is continuously displayed in the vertical direction of the screen 4*a*.

During the resection of the treatment target A, the operator controls the position and the movement direction of the treatment tool 5 on the basis of the treatment target A in the endoscope image D displayed on the screen 4*a*. With this embodiment, it is possible to continuously display, on the screen 4*a*, the treatment target A in a state in which it is easy for the operator to perform treatment regardless of deformation of the treatment target A during the resection.

In the case in which the area in which the endoscope 1 can be moved is restricted, there are cases in which the endoscope 1 cannot be moved to the target position and the target pose at which the three feature values become roughly equal to the respective references. For example, in the case in which the surgery system 100 is equipped with a function for preventing interference between the endoscope 1 and a peripheral object (for example, peripheral tissue or other instruments), the endoscope 1 cannot be moved to the position at which interference between the endoscope 1 and the peripheral object is predicted to occur. In such a case, the control device 3 may create, by processing the endoscope image D, an image in which the amounts of change in the three feature values from the respective references become zero and output the created image to the display device 4 so as to be displayed on the screen 4*a*. Accordingly, as with when the endoscope 1 is moved, it is possible to move and rotate the display area of the treatment target A displayed on the screen 4*a*.

Figure 7:
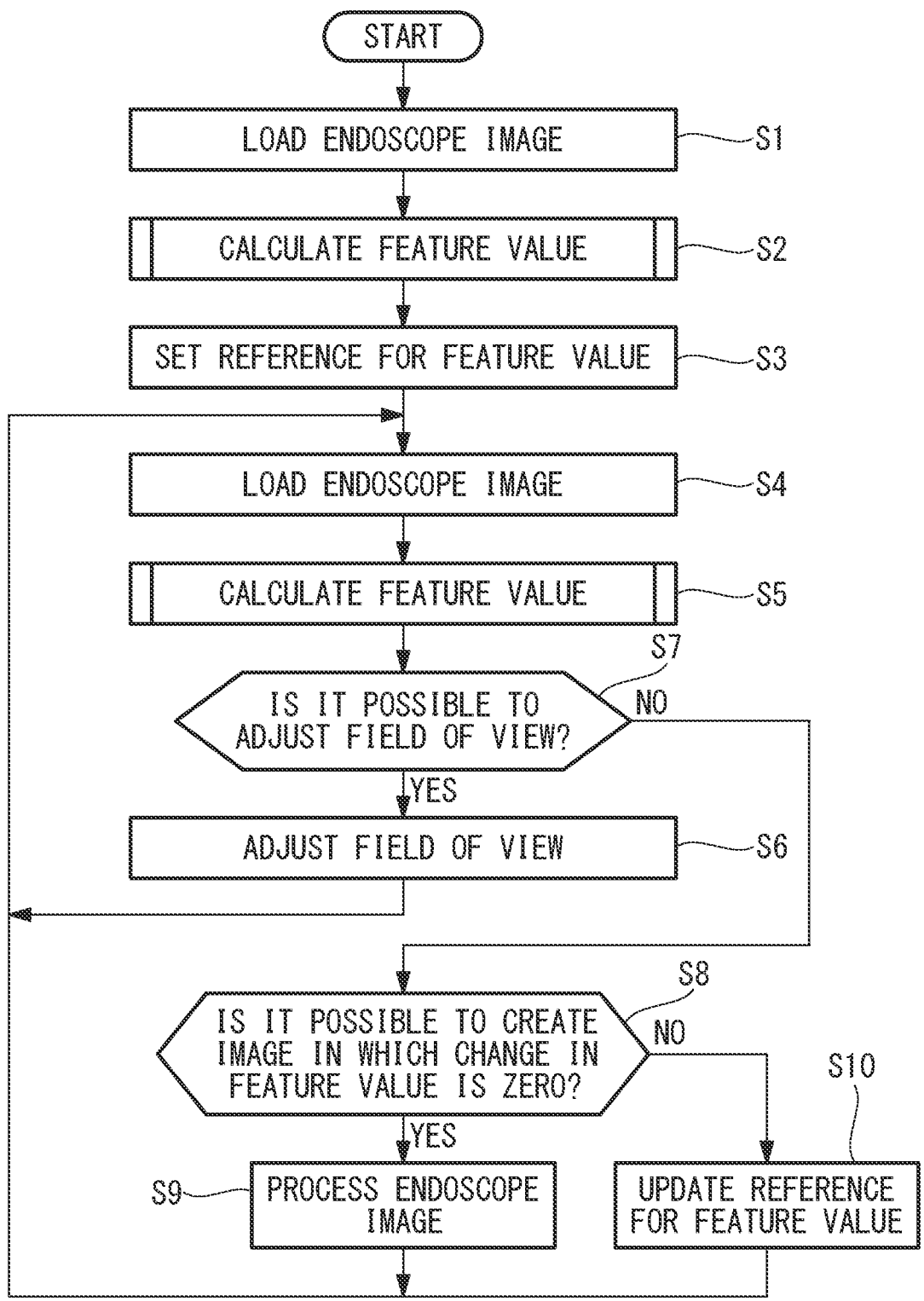
FIG. 7 is a flowchart of a modification of the control method in FIG. 5A.

Specifically, as shown in FIG. 7, steps S7 to S10 may be added after step S5.

In step S7, the control device 3 determines whether it is possible to move the endoscope 1 to the target position and the target pose. In the case in which it is determined that it is not possible to move the endoscope 1 to the target position and the target pose ("NO" in step S7), in step S8, the control device 3 determines whether it is possible to create an endoscope image D in which changes in the feature values are zero by means of image processing. In the case in which it is possible to create an endoscope image D in which changes in the feature values are zero by means of image processing ("YES" in step S8), the control device 3 performs the image processing in step S9. Specifically, the control device 3 creates an image in which amounts of changes in the feature values are zero by applying trimming, enlarging/shrinking, and rotating processing to the endoscope image D loaded in step S4.

In the case in which it is not possible to create an image in which changes in the feature values are zero by means of image processing ("NO" in step S8), the control device 3 may update the references for the feature values in step S10. For example, the control device 3 may set the feature values calculated in step S5 to be new references.

Figure 8:
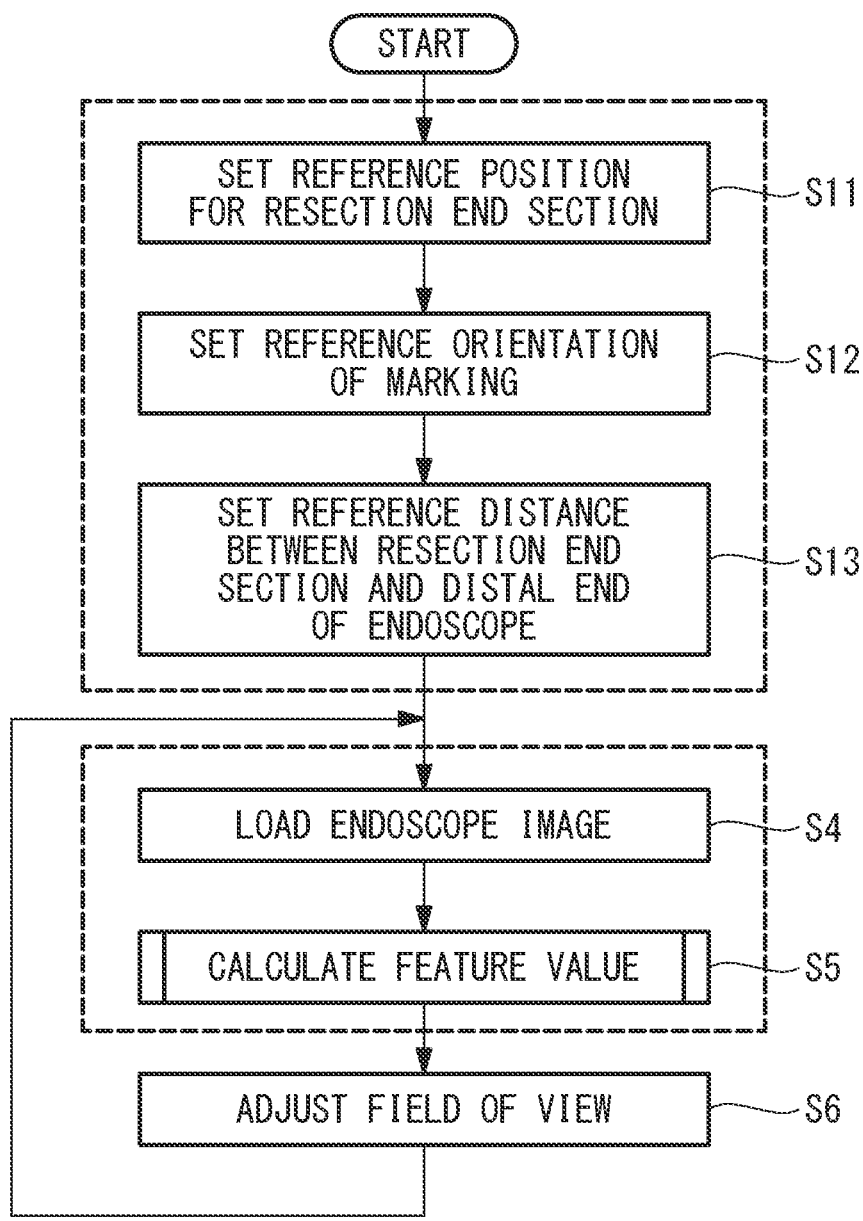
FIG. 8 FIG. 8 is a flowchart of a modification of the control method in FIG. 5A.
Figure 9:
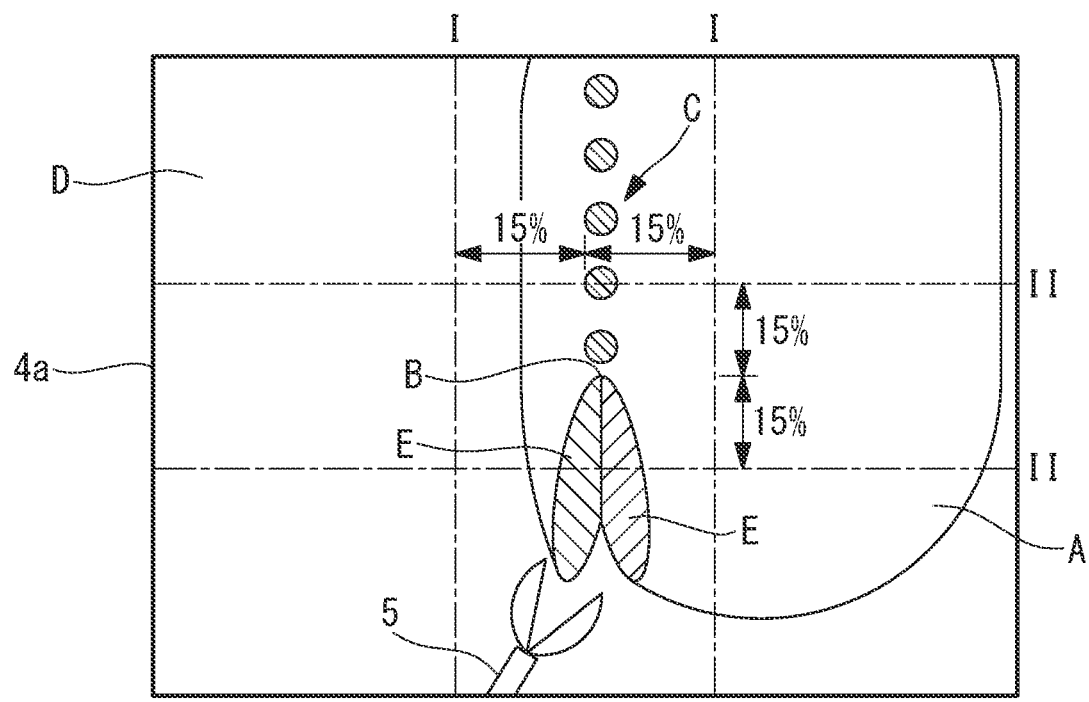
FIG. 9 FIG. 9 is a diagram for explaining another example of a reference position.

In the above-described embodiment, the feature values are calculated on the basis of the endoscope image D in advance before steps S4 to S6, and the feature values calculated in advance are set to be the references; however, alternatively, as shown in FIG. 8, the references may be set in advance. FIG. 9 shows examples of references set in advance for the first feature value and the second feature value.

The reference position that serves as the reference for the first feature value is set at one prescribed point or one prescribed portion on the screen 4*a* (step S11). The reference position may be a center point or a center region on the screen 4*a*. As shown in FIG. 9, it is preferable that the center region be within an area having dimensions corresponding to ±15% of the horizontal dimension of the screen 4*a* in horizontal directions from the center point and within an area having dimensions corresponding to ±15% of the vertical dimension of the screen 4*a* in vertical directions from the center point. The center region is not limited to a rectangular shape and may be, for example, a circular or oval region centered on the center point of the screen 4*a*.

The reference orientation that serves as the reference for the second feature value is set to be a direction in which, of two end sections of the marking C on the screen 4*a*, an end section far from the resection end section B is disposed within an area of ±15% in horizontal directions from the center point of the screen 4*a* (within an area indicated by I-I) (step S12). Accordingly, the marking C is maintained in a direction that is parallel to or substantially parallel to the vertical direction of the screen 4*a*. In order to maintain the marking C in the direction that is parallel or substantially parallel to the horizontal direction of the screen 4*a*, the reference orientation may be set in a direction in which the far end section of the marking C is disposed within an area of ±15% in vertical directions from the center point of the screen 4*a* (within an area indicated by II-II).

The reference distance that serves as the reference for the third feature value is set by means of the same methods as in steps S21, S22, S24 to S26, and S3, described above (step S13).

In the above-described embodiment, the intersection between the marking C and the edge F of the resected surface E is calculated so as to serve as the position of the resection end section B; however, the calculation method for the position of the resection end section B is not limited thereto, and said position may be calculated by other methods.

Figure 10A:
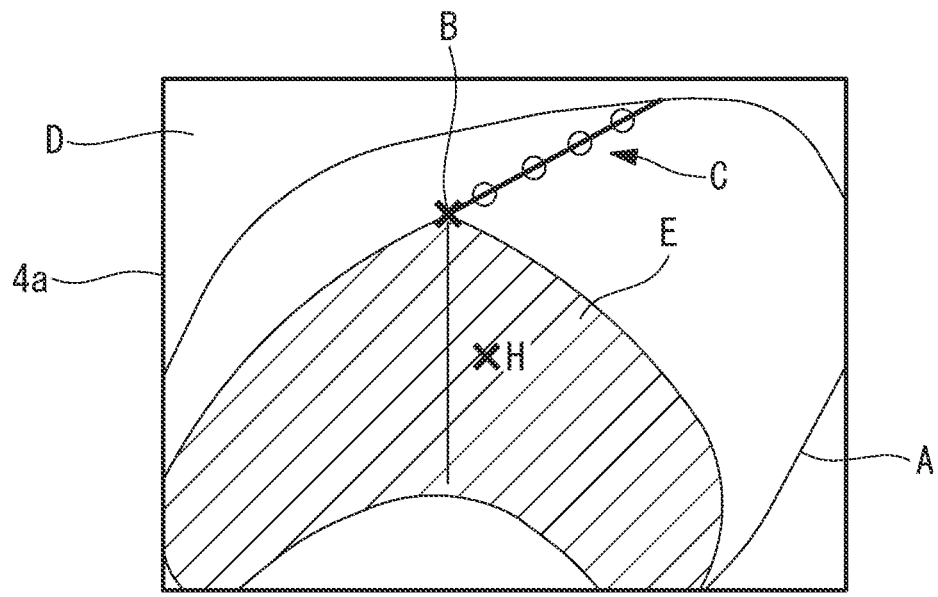
FIG. 10A is a diagram for explaining another calculation method for the resection end section.
Figure 10B:
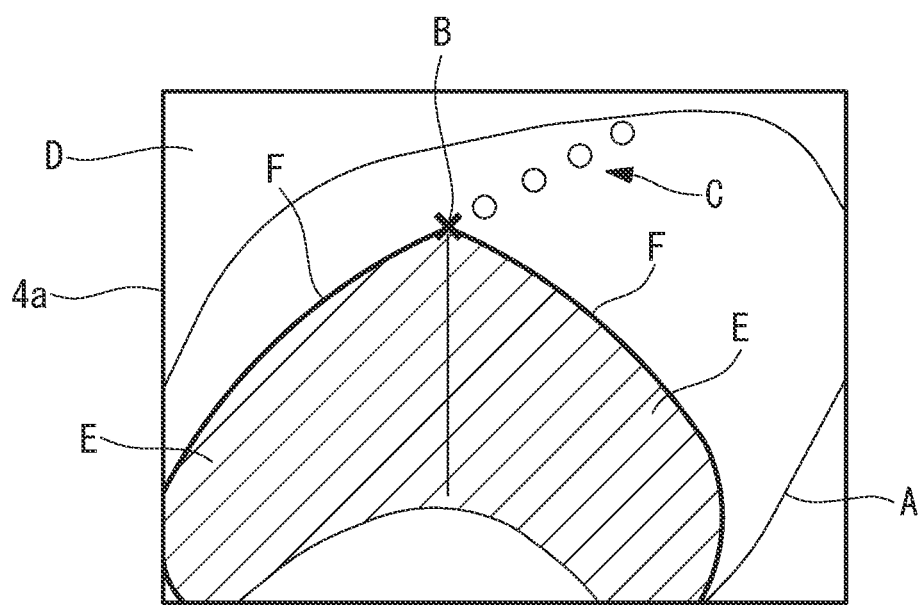
FIG. 10B is a diagram for explaining another calculation method for the resection end section.

FIGS. 10A and 10B show other examples of the calculation method for the resection end section B.

In FIG. 10A, the control device 3 calculates the position of the center of gravity H of the resected surface E and calculates, of the two end sections of the marking C on the screen 4*a*, the position of the end section close to the center of gravity H so as to serve as the position of the resection end section B.

In FIG. 10B, the control device 3 calculates the position of the intersection between an edge F of the resected surface E on one side and an edge F of the resected surface E on the other side so as to serve as the position of the resection end section B. Alternatively, the control device 3 may linearly approximate the edges F of the resected surfaces E on the respective sides and may calculate the position of the intersection of the two straight lines so as to serve as the position of the resection end section B.

The top-side edge F of the resected surface E is an upward convex curve, and the resection end section B is positioned at the apex of the edge F. Therefore, other methods capable of detecting the apex of the edge F may be employed. For example, the control device 3 may calculate the maximum point of the curve representing the edge F so as to serve as the position of the resection end section B.

In the above-described embodiment, the case in which the marking C is directly added to the treatment target has been described as an example; however, the marking C may be a virtual marking displayed so as to be superimposed on the endoscope image D. In other words, the marking C may be a marking that is displayed on the screen 4a by applying image processing to the endoscope image D. The marking C is formed by means of a publicly known technology on the basis of information about the treatment target and is displayed on the screen 4a by being superimposed on the endoscope image D.

In the above-described embodiment, the case in which the treatment target A is the liver and laparoscopic surgery for resecting liver parenchyma is performed has been described as an example; however, the treatment target A and the surgery to which the surgery system 100 is applied are not limited thereto, and it is also possible to apply the surgery system 100 to other treatment targets and surgeries.

For example, in sigmoidectomy, when separating the fascia from the sigmoid colon, a separation line could move in the abdominal cavity. In this case, the endoscope 1 can autonomously be moved so that the separation line is disposed at the position, the direction, and the distance that make it easy to perform treatment by causing the field of view of the endoscope 1 to follow the separation line in accordance with the progress of the separation.

In addition, the type of endoscope included in the surgery system 100 may be other than a laparoscope, and the surgery system 100 may be applied to an endoscopic surgery other than a laparoscopic surgery.

In the above-described embodiment, the display area of the treatment target A displayed on the screen 4a is moved and rotated by moving the endoscope 1; however, alternatively, the display area may be moved and rotated only by means of image processing.

For example, the endoscope 1 acquires an endoscope image D covering a large area, and a portion of the endoscope image D is displayed on the screen 4a. In this case, by moving and rotating the portion of the endoscope image D displayed on the screen 4a, it is possible to achieve the same operational effects as the case in which the endoscope 1 is moved.

The following aspects can be also derived from the embodiments.

An aspect of the present invention is a surgery system including: an image acquisition device that captures an image of a treatment target; a display device having a screen that displays the image of the treatment target captured by the image acquisition device; and a control device that controls a display area of the treatment target displayed on the screen, wherein the control device calculates a position of a resection end section of the treatment target on the basis of the image of the treatment target acquired by the image acquisition device, and causes the display area of the treatment target to be moved to a position at which the resection end section is disposed at a prescribed reference position on the screen.

With this aspect, the image of the treatment target is captured by the image acquisition device inserted into the body of a patient, and the image of the treatment target is displayed on the screen of the display device. An operator resects the treatment target by using a treatment tool inserted into the body of the patient while viewing the treatment target displayed on the screen. There are cases in which, as a result of the treatment target deforming as the resection progresses, the position of the resection end section with respect to the image acquisition device changes.

During the resection of the treatment target, the control device calculates the position of the resection end section on the basis of the image. In the case in which the position of the resection end section is displaced from the prescribed reference position on the screen, the control device causes the display area of the treatment target to be moved to the position at which the resection end section is disposed at the prescribed reference position on the screen. In other words, the display area is moved so as to follow the changing position of the resection end section and the resection end section is continuously disposed at the prescribed reference position on the screen. Accordingly, it is possible to continuously display the treatment position on the screen in a state that is appropriate for performing treatment regardless of deformation of the treatment target during the resection.

The above-described aspect may include a moving device that moves the image acquisition device, wherein the control device: calculates an amount by which the calculated position of the resection end section has changed from the prescribed reference position; and causes, by controlling the moving device, the image acquisition device to be moved to a position at which the amount of change becomes zero.

With this configuration, when the position of the resection end section changes due to deformation of the treatment target, the field of view of the image acquisition device, which is the display area of the treatment target, is moved to a position at which the resection end section is disposed at the prescribed reference position on the screen, as a result of the moving device moving the image acquisition device. In this way, by causing the field of view of the image acquisition device to automatically follow the changing position of the resection end section, it is possible to continuously display the resection end section at the prescribed reference position on the screen.

In the above-described aspect, the control device may calculate the position of the resection end section on the screen in advance before calculating the position of the resection end section of the treatment target and moving the display area, and set the position of the resection end section calculated in advance to be the prescribed reference position.

With this configuration, the position of the resection end section on the screen calculated before changes in the position of the resection end section due to deformation of the treatment target occur is set to be the prescribed reference position. Therefore, for example, the prescribed reference position can be set so that the resection end section is disposed at a position that makes it easy for the operator to resect the treatment target.

In the above-described aspect, the control device may set the prescribed reference position at an arbitrary position within a region of ±15% in vertical directions from a center of the screen and/or of ±15% in horizontal directions from the center of the screen.

With this configuration, it is possible to continuously display the resection end section in the center region of the screen.

In the above-described aspect, the control device may further: calculate an orientation of a marking added to the treatment target on the screen; and cause the display area of the treatment target to be rotated to an orientation in which the marking is disposed in a prescribed reference orientation on the screen.

There are cases in which a marking representing a planned resection line is added to the treatment target. There are cases in which the orientation of the marking also changes as the resection progresses as with the position of the resection end section. With the above-described configuration, during the resection of the treatment target, the control device calculates the orientation of the marking on the screen. In the case in which the orientation of the marking is displaced from the prescribed reference orientation on the screen, the control device causes the display area to be rotated to an orientation in which the marking is disposed in the prescribed reference orientation on the screen. In other words, the display area is rotated so as to follow the changing orientation of the marking, and the marking is continuously disposed in the prescribed reference orientation on the screen. Accordingly, it is possible to continuously display the treatment position on the screen in a state that is more appropriate for performing treatment regardless of deformation of the treatment target during the resection.

In the above-described aspect, the control device may calculate the orientation of the marking on the screen in advance before calculating the orientation of the marking, and set the orientation of the marking calculated in advance to be the prescribed reference orientation.

With this configuration, the orientation of the marking on the screen calculated before changes in the orientation of the marking due to deformation of the treatment target occur is set to be the prescribed reference orientation. Therefore, for example, the prescribed reference orientation can be set so that the marking is disposed in an orientation that makes it easy for the operator to resect the treatment target.

In the above-described aspect, the control device may set the prescribed reference orientation in an orientation in which, of two end sections of the marking, an end section far from the resection end section is disposed within a region of ±15% in vertical directions from a center of the screen or of ±15% in horizontal directions from the center of the screen.

With this configuration, it is possible to continuously display the marking on the screen so as to be substantially parallel to a vertical direction or a horizontal direction.

In the above-described aspect, the control device may calculate a position of an intersection between a marking added to an outer surface of the treatment target and an edge of a resected surface of the treatment target so as to serve as the position of the resection end section. Alternatively, in the above-described aspect, the control device may calculate, of two end sections of a marking added to an outer surface of the treatment target on the screen, a position of an end section closer to a center of gravity of a resected surface of the treatment target so as to serve as the position of the resection end section. Alternatively, in the above-described aspect, the control device may calculate a position of an intersection between edges of resected surfaces on two sides of the treatment target so as to serve as the position of the resection end section.

With these configurations, it is possible to calculate the position of the resection end section by means of simple image processing and calculations.

In the above-described aspect, the control device may cause the display area of the treatment target to be moved while a size of the display area of the treatment target is maintained.

For example, in the case in which the display area of the treatment target is moved by moving the image acquisition device, the size of the display area changes when the distance between the image acquisition device and the treatment target changes. With the above-described configuration, it is possible to eliminate such a problem and to continuously display the display area of the treatment target on the screen in a constant size.

In the above-described aspect, the control device may cause the display area of the treatment target to be moved by processing the image.

With this configuration, in the case in which the image acquisition device cannot be moved to the target position by means of the moving device, it is possible to continuously display the position of the resection end section at the prescribed reference position on the screen by applying image processing to the image. Alternatively, the moving of the display area can be realized only by means of the image processing without moving the image acquisition device.

In the above-described aspect, in a case in which the display area of the treatment target cannot be moved to a position at which the resection end section is disposed at the prescribed reference position on the screen, the control device may update the prescribed reference position.

With this configuration, in the case in which the area in which the image acquisition device can be moved is restricted, etc., there are cases in which it is not possible to move the resection end section to the prescribed reference position by moving the image acquisition device and by applying image processing to the image. In such a case, the prescribed reference position is updated; in other words, by setting a new prescribed reference position at another position on the screen, it is possible to continuously display the resection end section at the new prescribed reference position on the screen.

Another aspect of the present invention is a control method executed by a control device of a surgery system, the surgery system including an image acquisition device that captures an image of a treatment target and a display device having a screen that displays the image of the treatment target captured by the image acquisition device, and the method including: calculating a position of a resection end section of the treatment target on the basis of the image of the treatment target acquired by the image acquisition device; and causing a display area of the treatment target to be moved to a position at which the resection end section is disposed at a prescribed reference position on the screen.

REFERENCE SIGNS LIST 100 surgery system
1 endoscope (image acquisition device)
2 moving device, robot arm
3 control device
4 display device
4a screen
5 treatment tool
A treatment target
B resection end section
C marking
D endoscope image
G gravity

The invention claimed is:

1. A surgery system comprising:
a processor comprising hardware, wherein the processor is configured to:
set:
a prescribed reference position based on a position of a first resection end section in a first image displayed on a display screen, the first resection end section being a first intersection of a planned resection line denoted by a marking added to a treatment target and an edge of a resected surface of the treatment target; and
a prescribed reference orientation based on an orientation of the marking in the first image displayed on the display screen;
calculate:
a position of a second resection end section in a second image, the second resection end section being a second intersection of the planned resection line and the edge of the resected surface of the treatment target upon further resection; and
a second orientation of the marking in the second image;
determine at least one of an amount of movement or an amount of rotation of an imager to move the position of the second resection end section to the prescribed reference position and to rotate the second orientation of the marking to the prescribed reference orientation; and
adjust a position and an orientation of the imager based on the at least one of the amount of movement or the amount of rotation determined.

2. The surgery system according to claim 1, wherein the processor is configured to control a robot arm to adjust the position and the orientation of the imager based on the amount of movement and the amount of rotation determined.

3. The surgery system according to claim 1, wherein the processor is configured to calculate the position of the first resection end section in the first image displayed on the display screen.

4. The surgery system according to claim 1, wherein the processor is configured to set the prescribed reference position at a position within a region of ±15% in vertical directions from a center of the display screen and/or of ±15% in horizontal directions from the center of the display screen.

5. The surgery system according to claim 1, wherein the processor is configured to calculate the orientation of the marking in the first image displayed on the display screen.

6. The surgery system according to claim 1, wherein the processor is configured to set the prescribed reference orientation in an orientation in which, of two end sections of the marking in the first image displayed on the display screen, an end section further from the first resection end section is disposed within a region of ±15% in vertical directions from a center of the display screen or of ±15% in horizontal directions from the center of the display screen.

7. The surgery system according to claim 1, wherein the processor is configured to calculate, of two end sections of the marking in the first image displayed on the display screen, a position of an end section closer to a center of gravity of the resected surface of the treatment target so as to serve as the position of the first resection end section.

8. The surgery system according to claim 1, wherein the processor is configured to process the second image to adjust the position and the orientation of the imager based on the amount of movement and the amount of rotation determined.

9. A control method executed by a processor, comprising:
setting:
a prescribed reference position based on a position of a first resection end section in a first image displayed on a display screen, the first resection end section being a first intersection of a planned resection line denoted by a marking added to a treatment target and an edge of a resected surface of the treatment target; and
a prescribed reference orientation based on an orientation of the marking in the first image displayed on the display screen;
calculating:
a position of a second resection end section in a second image, the second resection end section being a second intersection of the planned resection line and the edge of the resected surface of the treatment target upon further resection; and
a second orientation of the marking in the second image;
determining at least one of an amount of movement or an amount of rotation of an imager to move the position of the second resection end section to the prescribed reference position and to rotate the second orientation of the marking to the prescribed reference orientation; and
adjusting a position and an orientation of the imager based on the at least one of the amount of movement or the amount of rotation determined.

10. The control method according to claim 9, wherein adjusting the position and the orientation of the imager comprises controlling a robot arm to adjust the position and the orientation of the imager based on the amount of movement and the amount of rotation determined.

11. The control method according to claim 9, further comprising:
calculating the position of the first resection end section in the first image displayed on the display screen.

12. The control method according to claim 9, wherein setting the prescribed reference position comprises setting the prescribed reference position at a position within a region of ±15% in vertical directions from a center of the display screen and/or of ±15% in horizontal directions from the center of the display screen.

13. The control method according to claim 9, further comprising:
calculating the orientation of the marking in the first image displayed on the display screen.

14. The control method according to claim 9, wherein setting the prescribed reference orientation comprises setting the prescribed reference orientation in an orientation in which, of two end sections of the marking in the first image displayed on the display screen, an end section further from the first resection end section is disposed within a region of ±15% in vertical directions from a center of the display screen or of ±15% in horizontal directions from the center of the display screen.

15. The control method according to claim 9, further comprising:

calculating, of two end sections of the marking in the first image displayed on the display screen, a position of an end section closer to a center of gravity of the resected surface of the treatment target so as to serve as the position of the first resection end section.

16. The control method according to claim 9, wherein the first resection end section is an intersection between edges of resected surfaces on two sides of the treatment target.

17. The control method according to claim 9, further comprising:
   determine whether the position and the orientation of the imager can be adjusted based on the amount of movement and the amount of rotation determined; and
   in response to determining that the position and the orientation of the imager cannot be adjusted based on the amount of movement and the amount of rotation determined, updating the setting of the prescribed reference position.

18. A surgery system comprising:
   an imager that captures an image of a treatment target;
   a display having a screen that displays the image of the treatment target captured by the imager; and
   a processor comprising hardware, the processor being configured to control a display area of the treatment target displayed on the screen, wherein the processor is configure to:
      calculate a position of a resection end section of the treatment target on the basis of the image of the treatment target acquired by the imager;
      cause the display area of the treatment target to be moved to a position at which the resection end section is disposed at a prescribed reference position on the screen;
      calculate an orientation of a marking added to the treatment target on the screen; and
      cause the display area of the treatment target to be rotated to an orientation in which the marking is disposed in a prescribed reference orientation on the screen,
   wherein the processor is configured to calculate, of two end sections of the marking on the screen, a position of an end section closer to a center of gravity of a resected surface of the treatment target so as to serve as the position of the resection end section.

19. The surgery system according to claim 18, where the processor is configured to control a robot arm to move the display area of the treatment target to the position at which the resection end section is disposed at the prescribed reference position on the screen and rotate the display area of the treatment target to the orientation in which the marking is disposed in the prescribed reference orientation on the screen.

20. The surgery system according to claim 18, wherein the processor is configured to calculate the prescribed reference position and the prescribed reference orientation.

* * * * *